United States Patent [19]

Burckhardt

[11] Patent Number: 4,687,003

[45] Date of Patent: Aug. 18, 1987

[54] DENTAL DEVICE

[76] Inventor: Rainer Burckhardt, Mühlweg 49, 8480 Weiden, Fed. Rep. of Germany

[21] Appl. No.: 859,652

[22] Filed: May 5, 1986

Related U.S. Application Data

[63] Continuation-in-part of Ser. No. 554,177, Nov. 22, 1983, abandoned.

[30] Foreign Application Priority Data

Nov. 26, 1982 [DE] Fed. Rep. of Germany ... 8233294[U]

[51] Int. Cl.$^4$ .......................... A61C 19/04; A61C 9/00
[52] U.S. Cl. .................................... 128/777; 128/782; 33/DIG. 3; 340/870.16
[58] Field of Search .................. 128/777, 782, 774; 33/174 D, DIG. 3; 340/870.16, 870.24, 870.29

[56] References Cited

U.S. PATENT DOCUMENTS 1,161,504  11/1915  Miller .............................. 33/174 D
3,922,654  11/1975  Hobson, Jr. ..................... 340/870.16
4,303,077  12/1981  Lewin et al. ....................... 128/777
4,447,207   5/1984  Kataoka et al. ................... 128/777

FOREIGN PATENT DOCUMENTS 1931004  1/1970  Fed. Rep. of Germany ...... 128/777
 232447  4/1969  U.S.S.R. ............................. 128/777

Primary Examiner—Andrew H. Metz
Assistant Examiner—Chung K. Pak
Attorney, Agent, or Firm—Jacobs & Jacobs

[57] ABSTRACT

The invention relates to a device for the three-dimensional determination of the movement between two bodies, in which the components of movement are determined by means of two measurement-value transmitters, each of which has a first transmitter element and a second transmitter element which are movable relative to each other. One transmitter element has, in this connection, at least one light path or measurement path within which a filter acting as dispersion screen is movable on the other transmitter element.

13 Claims, 13 Drawing Figures

DENTAL DEVICE

This is a continuation-in-part of my copending application Ser. No. 554,177 filed Nov. 22, 1983, now abandoned, the contents of which are incorporated herein by reference thereto.

The invention relates to a device for the three-dimensional determination of the relative movement between a first body and a second body, preferably to a device for the three-dimensional determination of the relative movement of the lower jaw or lower-jaw joints (condyles) of a patient, having at least two measurement transmitters arranged spaced apart from each other on said two bodies, each of which transmitters has a first transmitter element and a second transmitter element which is movable relative to the first transmitter element, the first transmitter elements being adapted to be fastened to the first body, preferably the lower jaw of the patient, and the second transmitter elements being adapted to be fastened to the second body, preferably the head of the patient, and having a total of at least five measurement paths on the second transmitter elements, two which measurement paths serve to determine the relative movement of the transmitter elements of said at least two measurement-value transmitters in a horizontal axis, two measurement paths serve to determine the relative movement of the transmitter elements of said at least two measurement-value transmitters in a vertical axis and at least one measurement path serves to determine the relative movement of the transmitter elements of said at least two measurement-value transmitters in the transverse axis, and at least one of said measurement paths is formed by a source of light and a light detector arranged at a distance from said source.

In industry in general the problem frequently arises of detecting (measuring) and recording three-dimensional movement between two bodies or elements. This problem is present in particular also in dentistry, where it is a question of measuring the movement of the lower jaw with respect to the upper jaw of a patient and recording the data obtained thereby. This is necessary, in particular, when the movement of the jaw is to be simulated in a so-called "articulator", for which purpose it is necessary to determine on the patient the specific position and movement of the lower jaw with respect to the upper jaw and transmit the values obtained in this way to the articulator ("transmission").

In particular, for the three-dimensional determination of the movement of the lower-jaw joints in the vertical, horizontal and lateral or transverse axes (axes of the jaw joints) devices have already been proposed, in some of which the paths of movement are recorded mechanically on recording plates by means of recording styli. These devices are cumbersome to handle and give only very inaccurate results. Devices have also been proposed in which the components of movement are determined by means of measurement paths which either have electromechanical transducers (wire strain gauges or variable resistors) and do not operate free of contact any more than the first-mentioned known devices do, or else employ opto-electrical methods, in which case the components of movement are determined on basis of a varying light-reflection angle. These known devices are also relatively complicated in construction, do not provide measurement data of the high accuracy desired and, in particular, require a relatively long period of time for fastening and adjustment on the patient as well as for the transmission of the data obtained to an articulator.

The object of the invention is to provide a device which, while being of simple construction and simple to operate, permits accurate and rapid three-dimensional determination of the relative movement between two bodies, the fastening in proper position and the adjustment of the device to the reference position necessary for the measurement being also possible without any problems.

In order to achieve this purpose, a device of the aforementioned type is so developed that in order to form at least one light path on at least one of the second transmitter elements a source of light and, spaced from and opposite it, a light detector are provided on the same transmitter element, and that the first transmitter element which cooperates with this second transmitter element is at least in part a filter which is developed as a dispersion screen and lies within the light path.

By "dispersion screen", as used in the invention, there is to be understood a filter (or filter region) which (referred to a given cone of light for the light radiated by the source of light) produces a greater or lesser dispersion of the light emitted by the source of light upon movement along the connecting line between source of light and light detector, so that the quantity of light striking the light detector is dependent on the instantaneous position of the dispersion screen (distance from the source of light or from the light detector). Movement of the dispersion screen in the direction transverse or perpendicular to the connecting line between source of light and light detector causes no change in the amount of light striking the detector and thus also no change in the signal given off by the light detector. With the measurement path or light path which contains the dispersion screen it is therefore possible to measure in very simple manner those components of movement which take place in that axis in space which corresponds to the light path.

The components of movement in the two other axes in space are also preferably determined electro-optically in the measuring device of the invention, in the manner that the second transmitter element of each measurement-value transmitter has two additional light path or measurement paths having a source of light and a light detector, a transmission wedge being arranged in each of these light paths.

By "transmission", as used in the invention, there is to be understood a filter (or filter region) which has increasing filter density in a given axial direction lying within the plane of the filter, so that upon the movement of the filter in said axial direction perpendicularly or transversely to the connecting line between source of light and light detector, the amount of light striking the light detector, and thus also the signal given off by the light detector, change, whereas movement of the transmission wedge in the direction of the connecting line between source of light and light detector causes no change in the signal given off by the detector. The change or variation of the filter density is preferably so selected in the transmission wedges that the transmission of the filter changes with the movement of the filter transversely or perpendicularly to the connecting line between the source of light and light detector.

In principle, the two transmission wedges are then arranged in such a manner that their axial directions in which the filter density increases are perpendicular to each other and perpendicular to all the light paths on a measurement-value transmitter so that, by means of two light paths, each having a transmission wedge and a light path with dispersion screen, components of movement in three axes in space (vertical, horizontal and transverse or lateral axes in space) can be determined, although all the measurement paths lie parallel to each other in the direction of a single axis in space and the filters used are also arranged either in a common plane or else in several planes parallel to each other. In this way a particularly simple construction is obtained as well as the possibilty of particularly simple alignment of the device. If the device is used, for instance, for the three-dimensional determination of the movement of a lower jaw joint and if the light path or measurement path provided with the dispersion screen is used for determination of the transverse component of movement (in the direction of the axis of the jaw joint), then, in principle, it is sufficient to provide a light path with dispersion screen only on one measurement-value transmitter, although the use of such a measurement path on both measurement-value transmitters offers particular advantages with respect to minimizing errors in measurement.

In one preferred embodiment of the device of the invention, each of the measurement paths is formed by its own source of light and a corresponding light detector, it being also possible, in principle, to provide one source of light common to several measurement paths. In order to avoid falsification of the result of the measurement by ambient light, sources of light which emit light in the infrared region are preferably employed.

All filters (transmission wedges or dispersion screens) which are provided on the first transmitter element of a measurement-value transmitter are preferably formed of different filter regions of a single filter screen.

When the device is used for the three-dimensional determination of the relative movement of the lower jaw joints, this device has a lower yoke with two side arms which is adapted to be fastened to the lower jaw as well as an upper yoke, also having two side arms, which is adapted to be fastened to the head, one side arm of the upper yoke together with one side arm of the lower yoke forming a pair of side arms, the second transmitter element being provided preferably on each side arm of the upper yoke and the corresponding first transmitter element on each side arm of the lower yoke. It has also been found that the adjustment or alignment of the device on the head of the patient can be effected particularly easily if each of the second transmitter elements having the light paths is fastened to the corresponding side arm in a manner adjustable along two axes in space which are perpendicular to each other, and preferably in the direction of the longitudinal length of the side arm in question as well as in the direction perpendicular thereto or perpendicular to the plane determined by the two side arms, the adjustment prior to the measuring process itself being preferably effected in the manner that the at least one light path having the dispersion screen coincides, as accurately as possible, with the axis of the jaw joint or at least intersects said axis. This adjustment can be effected or checked very accurately by specific movements of the lower jaw and observation of the individual signals supplied by the measurement paths. The said possibility of adjustment of the second transmitter element is generally important, regardless of how the determination or measurement of the components of movement is effected.

Further developments of the invention form the subject of the subordinate claims. The invention will be explained in further detail below, with reference to an embodiment shown in the figures, in which:

The device for the three-dimensional determination of the movement of the lower jaw or lower-jaw joint which is shown in the figures consists essentially of an upper yoke 1 which can be fastened to the head of the patient 2 and of a lower yoke 3 which can be fastened to the lower jaw.

The upper yoke 1 is formed by a crossbar 4 and two side arms 5 and 6, one end of each of said arms being fastened to the crossbar and extending transversely or perpendicularly to said crossbar so that the crossbar 4 and the side arms 5 and 6 form an eyeglass-frame-like arrangement.

In the center, a profiled roller 7 is fastened for rotation and/or translation on the crossbar 4, said profiled roller having an annular recess whose cross-sectional profile varies around the circumference of the roller 7 in such a manner that the said cross-sectional profile can be adapted, by turning the profiled roller 7, to the cross-sectional profile of the nose 2' of the patient 2.

Figure 1:
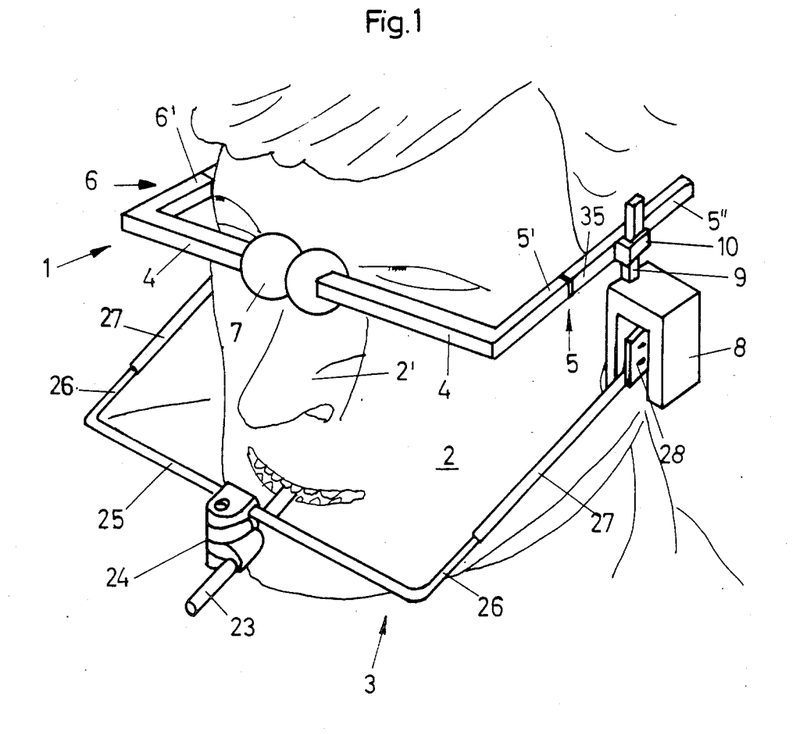
FIG. 1 shows, in perspective, one possible embodiment of the device for the three-dimensional determination of the movement of the lower jaw, after attachment to the head of the patient.
Figure 2:
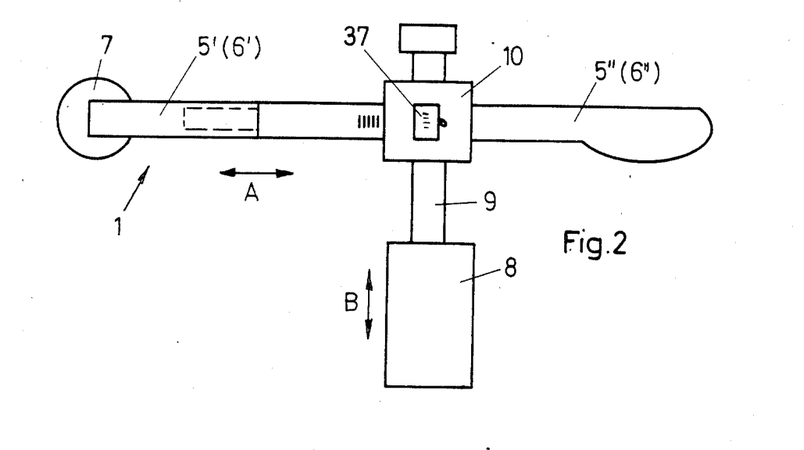
FIG. 2 shows, in side view, the upper yoke of the device according to FIG. 1.

As shown in particular in FIGS. 1 and 2, each of the two side arms 5 and 6 consists of two parts 5' and 5" and 6' and 6" respectively which are connected together in such a manner that adjustment of the parts 5' and 5" and 6' and 6" respectively relative to each other in the direction of the longitudinal axis of the side arm is possible, as indicated by the double-ended arrow A in FIG. 2.

The adjusting of the two parts 5' and 5" and 6' and 6" respectively is effected basically in the manner that one of the two parts engages into a guide within the other part. The two parts can, for instance, be developed for telescopic insertion one within the other. Once the adjustment has been effected, the two parts 5' and 5" and 6' and 6" respectively can be fixed in position by means not shown in detail, for instance clamps.

As furthermore shown in FIGS. 1 and 2, the ends of the parts 5' and 6' which are remote from the parts 5" and 6" respectively are connected to the crossbar 4, which connection can also be developed so as to be adjustable. On each of the parts 5" and 6" a corresponding transmitter element 8 is fastened in such a manner that, as seen in FIGS. 1 and 2, this element is located below the corresponding side arms 5 and 6 respectively.

Each of the two elements 8, which have the measurement paths for determining the movement of the lower jaw or lower-jaw joint in the horizontal, vertical and transverse axes, is held by an auxiliary arm 9 on the part 5" and 6" respectively in the embodiment shown, the arrangement being such that each element 8 can be adjusted relative to the side arm 5 or 6 respectively in the direction perpendicular to the lengthwise direction of the corresponding side arm 5 and 6 respectively as well as in the direction perpendicular to the plane formed by the side arms (in the direction indicated by the double-ended arrow 8 in FIG. 2). In the embodiment shown, this result is obtained in the manner that the corresponding auxiliary arm 9 is guided adjustably in lengthwise direction within a guide 10 on the part 5" and 6" respectively. Once the adjustment has been made it can, in this case also, be fixed by means not shown in detail.

As shown in FIG. 2, each element 8 is of substantially U shape and consists of two limbs or limb-like sections 11 and 12 which are connected to each other by a yoke 13. The arrnagement is such that the space 14 defined by the sections 11, 12 and 13 is open towards the bottom as well as towards two sides, which are perpendicular to the axis indicated by the double-ended arrow A. The arrangement is furthermore such that the section 12 of each element 8 on one side arm (the side arm 5) is closer to the other side arm (for instance the side arm 6) than the section 11 of this element is.

Figure 3:
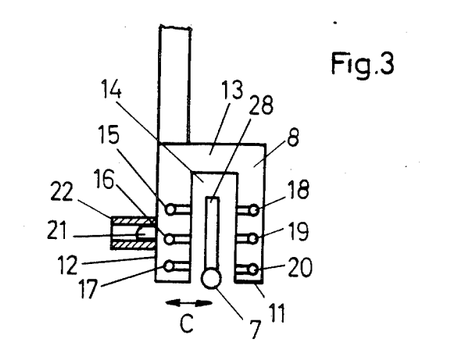
FIG. 3 shows, in a partial view turned 90° from the position in FIG. 2, a transmitter element which has a total of three measurement paths and is arranged on the side arm of the upper yoke of the device shown in FIG. 1.

In embodiment shown, three light sources 15, 16 and 17 are arranged one above the other in the direction of the axis characterized by the double-ended arrow B in the section 12 of each element 8, said sources of light preferably emitting light within the infrared region into the space 14, a light detector 18 being arranged opposite the source of light 15, a light 19 opposite the source of light 16, and a light detector 20 opposite the source of light 17 in the section 11 of each element 8 in such a manner that each source of light, together with its corresponding detector, forms a light path or measurement path which extends along an axis which is perpendicular to the two axes indicated by the arrows A and B and is characterized by the double-ended arrow C in FIG. 3. The sources of light 15, 16 and 17 are, for instance, light-emitting diodes while the light detectors 18, 19 and 20 are photodiodes, photoresistors or phototransistors. In principle, it is possible to dispense in one element 8 with that measurement path for the component of movement in the direction of the jaw-joint axis which is formed by the source of light 16 and the detector 19 and is arranged between the other two measurement paths, although the use of such a measurement path on both elements 8 permits a method of measurement by which this component of movement can be determined far more accurately.

In the embodiment shown, a source of light 21 which emits light in the visible region is provided on each element 8 on the outer surface of the section 12 facing away from the space 14. This source of light is arranged within the internal bore of a sleeve-like element 22 which protrudes from said surface of the section 12 facing away from the space 14. The arrangement is such that the source of light 21 produces on a surface lying adjacent to the sleeve-like element a spot of light which can serve to mark the hinge axis of the jaw joint on the head of the patient.

In the embodiment shown, a bite fork or a spoon 23 serves to fasten the lower yoke 3 to the lower jaw, which bite fork or spoon can be fastened to the row of teeth there by, for instance, a rail, not shown in detail. The free end of the spoon 23 is fastened via a double clamp 24 to the central region of a crossbar 25 of the lower yoke 3. This crossbar is provided at each of its ends with a section 26 which is bent off at a right angle, bar-like elements 27 having their one end held in removable fashion on said bent portions and being adjustable preferably in longitudinal and vertical directions. The bar-like elements 27 form the two side arms of the lower yoke 3.

Figure 4:
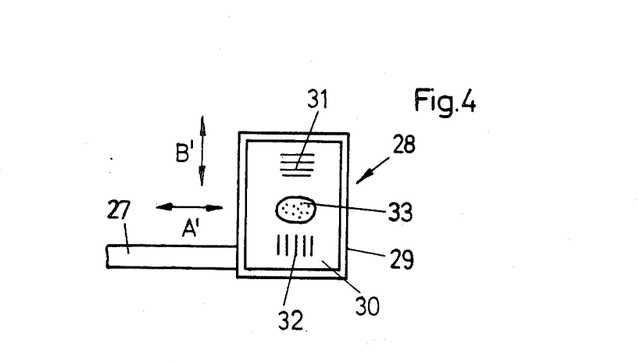
FIG. 4 shows, in a partial side view, one end, provided with a filter screen, of a side arm of the lower yoke.

At its end remote from the crossbar 25, each element 27 bears a filter 28 which, as shown in FIG. 4, is formed essentially of a frame 29 and a filter glass 30 arranged therein.

Each filter 28 has at least two filter regions 31 and 32 which act as absorption or transmission filters (transmission wedges) and each of which has a filter density which increases in an axial direction lying in the filter plane. These axial directions are indicated in FIG. 4 by the double-ended arrows A' and B', the filter density of the filter region 21 increasing in the axial direction indicated by the double-ended arrow B' and the filter density of the filter region 32 increasing in the axial direction indicated by the double-ended arrow A'. The two filters 28 furthermore also have a third filter region 33 which acts as dispersion filter or dispersion screen and is arranged between the filter regions 31 and 32.

The use of the device shown can be described as follows:

The upper yoke 1 is placed, as shown in FIG. 1, on the head of the patient in such a manner that the crossbar 4 rests on the nose 2' via the roller 7, while the side arms 5 and 6 rest in the manner of eyeglass temple-pieces with their free ends resting against the region of the ears of the head of the patient 2 and on his ears. After the spoon 23 has been fastened on the lower jaw of the patient 2, the lower yoke 3 is fastened to this spoon. The elements 27 are then placed on the backward bent parts 26 of the crossbar 25 in such a manner that the filter 28 of each element 27 extends into the space 14 of an element 8, with its filter surface being as perpendicular as possible to the axis characterized by the double-ended arrow C, it being seen to it, possibly by suitable adjustment of the elements 8 and/or by suitable adjustment of the elements 27 and/or by suitable adjustment of the crossbar 27 on the spoon 23, that the filter region 31 of each filter 28 is arranged in the region of light path formed by the source of light 15 and the arranged 18, the filter region 32 of each filter is arranged in the region of the light path formed by the source of light 17 and the detector 20, and the filter region 33 is arranged in the region of the light path formed by the source of light 16 and the detector 19 of an element 8, and that furthermore the axial directions A' and B' are substantially in the direction of the axes which are indicated by the double-ended arrows A and B. In order to obtain an unequivocal reference value for the three-dimensional determination of the movement of the lower jaw and be able to subsequently transmit the position of this lower jaw and of the upper jaw referred to the jaw joints to an articulator, the axis of the hinge joint of the lower jaw is first of all determined. This is effected in the manner that the patient 2 moves his lower jaw relative to his head so as to carry out an opening and closing movement of his mouth. As a result, the filters 28 are moved relative to the elements 8 in the light paths or measurement paths, so that the light detectors give off signals which are displayed as components of movement in the horizontal axis (arrow A), in the vertical axis (arrow B) and in the transverse axis (arrow C) in an electrical measuring and evaluation device, not shown in detail, which is connected to said detectors. By corresponding adjustment of the two elements 8 relative to the side arms 5 and 6, it is then seen to it that upon simple opening and closing of the mouth no components of movement around the horizontal and vertical axis are displayed any longer. As soon as this condition has been reached, the sources of light 21, as well as the light paths formed by the sources of light 16 and corresponding light detectors 19, are precisely at the two ends of the hinge axis of the jaw joint. These two ends can then be marked on the skin of the patent in the region of the joint by means of the light spot produced by the light rays 21.

After the above-described adjustment of the device, the movement of the lower jaw, i.e. the corresponding displacement of the hinge axis upon chewing movements, etc., can be determined, the corresponding values being displayed and/or stored by the measurement and evaluation device.

As a result of the change in light transmission upon the movement of the filters 28, the light detectors 18, in combination with the filter regions 31, supply the vertical components of the movement of the lower jaw, while as a result of the change in light transmission upon movement of the filter 28, the light detectors 20, in combination with the filter regions 32, supply signals which correspond to the horizontal components of the movement of the lower jaw. The transverse component of the movement of the lower jaw, i.e. the component of movement in the direction of the hinge axis, is determined with the aid of the light detectors 19 in combination with the filter regions 33 in the manner that these filter regions, depending on the distance of the filter 28 from the source of light 16 and from the detector 19, cause a greater or lesser scattering of the light, so that the signal given off by the detector 19 is a measure of the movement of the corresponding filter 28 in the direction indicated by the double-ended arrow C, said axis coinciding essentially with the hinge axis after the adjustment of the device in the manner described above.

Figure 9:
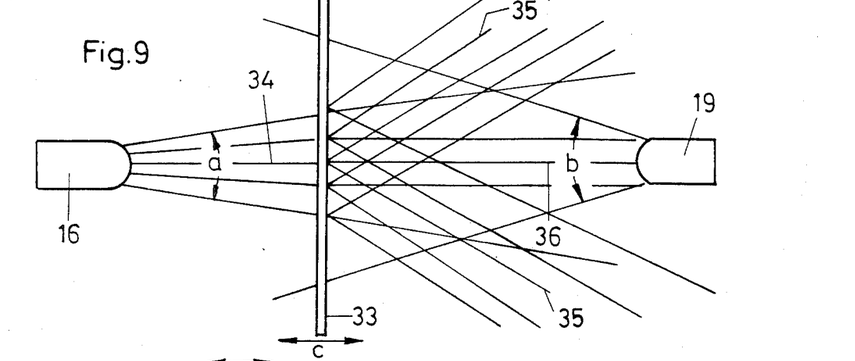
FIGS. 9 to 11 are different diagrams serving to explain the action of the dispersion screen.
Figures 10, 11:
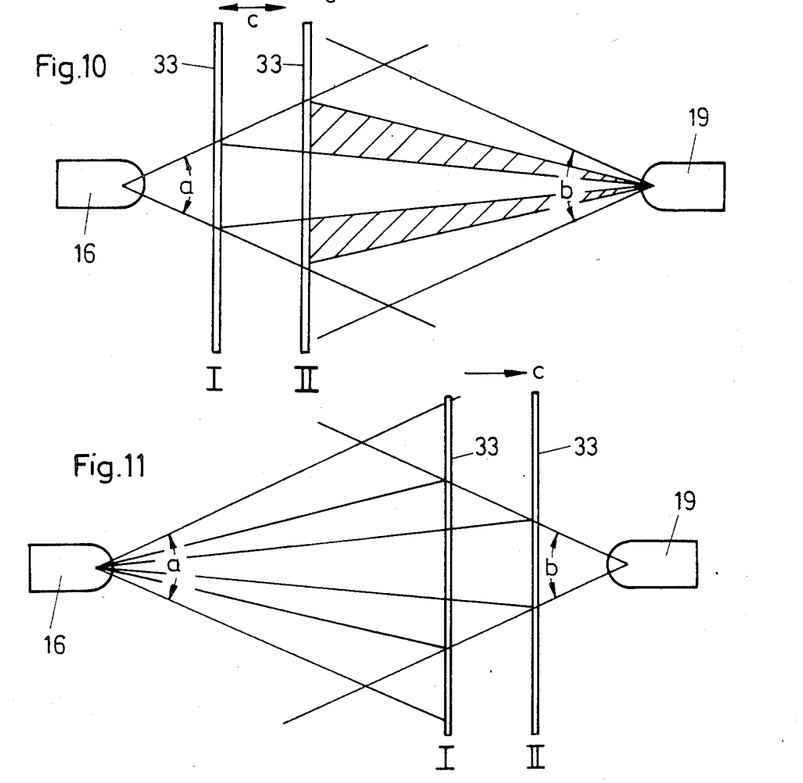

The manner of action of the measurement paths 16–19 having the filter regions 33 (dispersion screen) can be clearly noted from FIGS. 9 to 11, in which the source of light 16 and the corresponding detector 19 are diagrammatically shown together with the filter region 23 which acts as dispersion screen. The source of light 16 is developed in such a manner that an angle a results for the emerging cone of light, while the detector 19 has an aperture angle b. FIG. 9 shows that the light beam 34 which initially emerges focussed or as cone of light from the source of light 16 is in part dispersed by the dispersion screen 33 (dispersed light beams 35), the detector 19 not detecting the dispersed light beams 35 but only detecting the light beams 36 which strike the detector 19 after emergence from the dispersion screen 33 and are less intense than the light beams 34. The illuminated area lying within the aperture angle b of the detector which is produced by the light beams 34 on the dispersion screen 33 is an approximate measure of the intensity of the light detected by the detector 19.

FIG. 10 shows the case in which the dispersion screen 33 is closer to the source of light 16 than to the detector 19. If the dispersion disk is moved from the position designated I in FIG. 10 to the position II, in a manner corresponding to the arrow C, the intensity of the light impinging on the detector 19 changes in accordance with the hatched region shown in FIG. 10. Conditions are similar when the dispersion disk 33 is arranged in the vicinty of the detector 19 (FIG. 11). If the dispersion screen is moved in said figure from position I to position II (corresponding to the arrow C), then, with due consideration of the aperture angle b, there is a change in intensity of the light impinging on the detector 19, this change also corresponding to the hatched region. It has been found that the very linear dependence can be obtained between the distance of the dispersion screen 33 from the source of light 16 and the signal produced by the detector 19 whether the dispersion screen 33 is arranged in the left-hand or the right-hand half of the measurement path 16–19. Only with an arrangement directly in the central region would this dependence not be linear.

Since only the light path or measurement path formed by the source of light 16 and the detector 19 lies precisely in the region of the hinge axis of the jaw joint after the adjustment of the device, while the other two light paths are shifted with respect to the hinge axis, certain measurement errors are theoretically possible. Since the sources of light 15 and 17 as well as the corresponding light detectors 18 and 20 can, however, be arranged very close to the measurement path 16–19, such purely theoretical measurement errors are thus small and therefore without practical importance.

Figure 5:
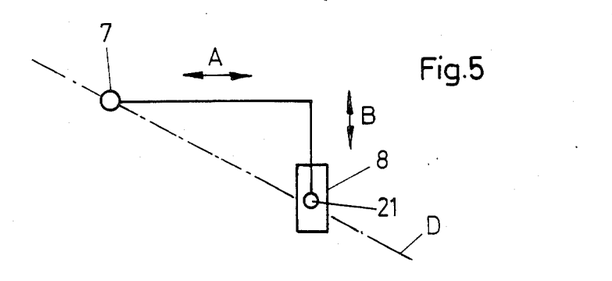
FIG. 5 is a diagram which serves to explain the possibility of adjustment of the transmitter element of FIGS. 2 and 3 along two axes which are perpendicular to each other (for instance the horizontal and vertical axes)

In order to obtain optimal measurement results, as well as to simplify the adjustment of the device, it is advisable to develop the filter regions 31 and 32 and the varying filter density of these regions in such a manner that upon movement of the filters 28 in the light paths a transmission of light results which increases and decreases linearly with the movement of the filter 28 in the vertical and horizontal axes respectively. By means of reading or adjustment scales 37 and 38 the displacement of the elements 8 in the two axes A and B referred to a reference value can be determined, it then also being possible to determine and/or indicate the reference plane characterized by D in FIG. 5 which is frequently used in practice and is determined by the point at which the roller 7 rests on the nose 2' and the two ends of the hinge axis.

Figures 6, 7, 8:
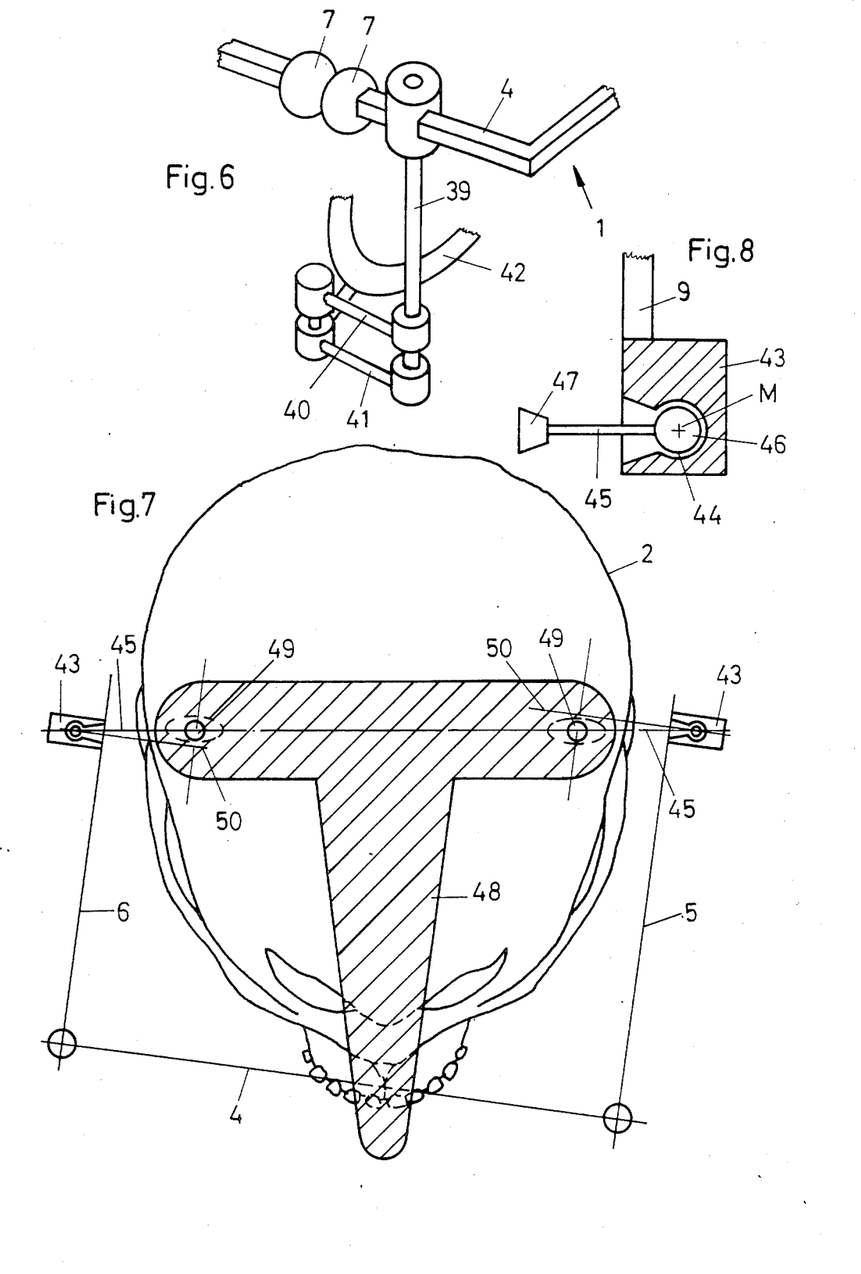
FIG. 6 is a partial view in perspective of the upper yoke with a bite fork fastened to it for fixing the position of the upper yoke with respect to the upper jaw of the patient.
FIG. 7 is a diagram showing, in top view, the head of the patient together with that part of the articulator which serves for positioning the rows of teeth of the upper jaw on the articulator.
FIG. 8 is a side view, in section, of a holding block which is used for the "transmission" to the articulator instead of the second transmitter elements.

In order to fix the position of the upper jaw and of the rows of teeth there with respect to the jaw joints in such a manner that the corresponding transmission to an articulator can take place at the same time by means of the upper yoke 1, a vertical bar 39 is fastened—in the development shown in FIG. 6—to the crossbar 4, said vertical bar hearing on its downward extending end, via connecting rods 40 and 41, a spoon or bite fork 42 for the upper jaw. With this development, the two elements 8 are preferably fastened in removable manner to the auxiliary arm 9, for instance by screws, not shown in detail, and can be replaced in each case by a holding block 43 so that then each auxiliary arm 9 bears such a block 43. Each holding block 43 has a recess 44 on the side thereof facing the head of the patient 2 or the other side arm, one end (ball 46) of a rod 45 being held in the manner of a ball joint in said recess, the development and attachment of the holding block 43 on the auxillary arm in question being of such a nature that the center point M of the ball joint lies at a point in space which, prior to the replacement of the element 8 by the holding block 43, was between the source of light 16 and the detector 19. At its other end, each bar 45 has a holding or coupling piece 47 by which the bar 45 can be fastened to a point of the articulator which corresponds to the axis of the jaw joint.

In FIG. 7, the upper yoke 1, the two holding blocks 43 fastened to it, the bars 45 as well as a holding plate 48 of an articulator are shown diagrammatically, together with a showing of the head of the patient 2.

Furthermore, in FIG. 7 the simulations 49 of the jaw joints on the articulator are also indicated. The lines 50 indicate the course which the measurement paths 16/19 would in themselves have with the adjustment effected of the upper yoke and the element 8. Since the two ends of the jaw-joint hinge axis lie on the said two measurement paths and/or, after the replacement of the elements by the holding blocks 43, are determined by the center points M while the axes of the measurement paths 16/19 (lines 50) do not necessarily lie, as shown in FIG. 7, coaxially with the hinge axis, a "transmission" in correct position to the articulator is possible by means of the bars 45 having the ball joints 44/46. It is obvious that resting surfaces or coupling elements for the resting or coupling pieces 47 are provided on the articulator or on the plate 48 provided there in the region of the simulations 49 for the jaw joints. By means of the holding blocks 43 which are provided with the bars 45 the transmission to the articulator is greatly simplified and is very precise, even with an asymmetric adjustment of the elements 8 or the holding blocks 43.

Figure 12:
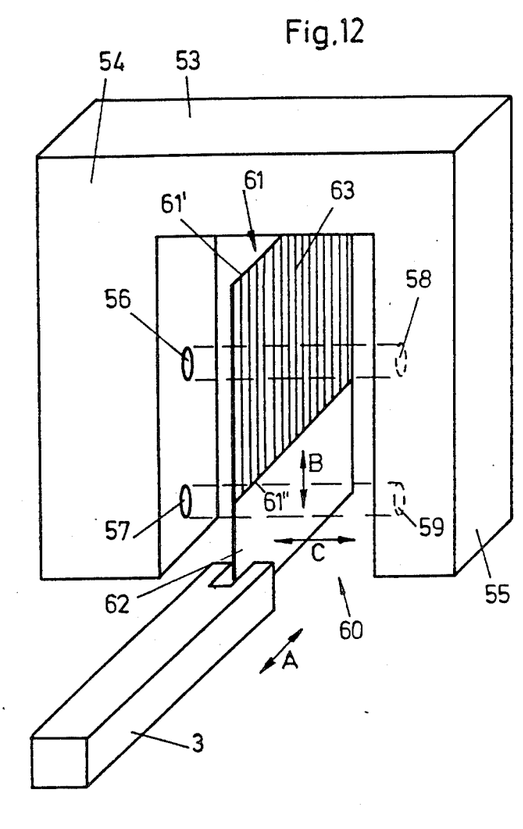
FIG. 12 shows, in diagrammatic perspective view, an alternative embodiment of the measurement transmitter of the apparatus according to the invention.
Figure 13:
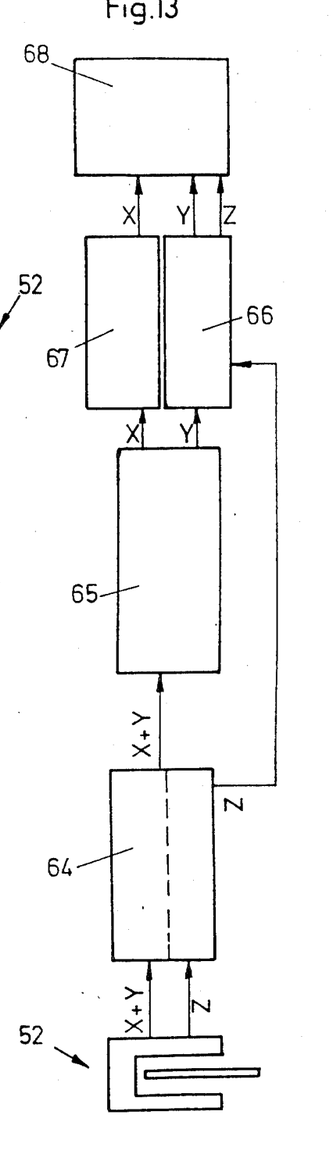
FIG. 13 shows the measurement transmitter of FIG. 12 together with a block diagram of an electric circuit for the evaluating or decoding of the electric signals supplied by the measurement transmitter.

With reference to FIGS. 12 and 13, measurement transmitter 52 comprises the transmitter element 53 which is developed in U shape similar to the transmitter element 8 and has two arms 54 and 55. On the side of the arm 54 facing the arm 55, there are provided two sources of light 56 and 57 which emit infrared light. Two light detectors 58 and 59, for example, photodiodes, photoresistors or phototransistors, are provided on the arm 55 in such a manner that the light detector 58 is opposite the source of light 56 and the light detector 59 is opposite the source of light 57, so that two light paths are formed, each having a source of light and a light detector.

The measurement transmitter 52 also has a transmitter element 60 which is formed of two optical filters or filter regions 61 and 62. The filter region 62, which lies in the light path between the source of light 57 and the light detector 59, acts again as a dispersion filter or dispersion disk and therefore corresponds to the filter region 33, so that the source of light impinging on the light detector 59 changes, as a function of the movement of the transmitter element 60, in the direction of the arrow C, i.e. in the direction perpendicular to the common plane of the two filter regions 60 and 62, as has been described above for the filter regions 33. The electric output signal Z of the light detector 59 thus corresponds to the movement of the transmitter element 60 relative to the transmitter element 53 in the axial direction indicated by the arrow C and is an analog measurement signal.

The filter region 61 lying in the light path between the source of light 56 and the light detector 58 is developed as an absorption or transmission filter (transmission wedge) and has a filter density which increases in the axial direction indicated by the double-ended arrow B, i.e. in the embodiment shown, the filter density increases from the upper edge 61' to the lower edge 61" of the rectangularly developed filter region 61, namely in each cause in the same manner over the entire width extending in the direction of these edges.

The filter region 61 furthermore has a line raster which is formed of a plurality of lines 63 which extend parallel to each other and perpendicular to the edges 61' and 61", and thus also perpendicular to the axis indicated by the double-ended arrow A. Upon relative movement of the transmitter element 60 with respect to the transmitter element 53 in the direction of the double-ended arrow B, the light impinging on the light detector 58 changes, and thus also the electric output signal Y given off by the light detector 58, in a manner corresponding to the filter density of the filter region 61, so that the output signal of the light detector 58 correponds to the relative movement in the direction of the double-ended arrow B, doing so in the form of an analog measurement signal.

Upon movement of the transmitter element 60 relative to the transmitter element 53 in the direction of the double-ended arrow A, the lines 63 of the line raster move through the light path between the source of light 56 and the light detector 58, so that the luminous flux impinging on the light detector 58 is in each case briefly interrupted or strongly reduced (upon the movement of the line 63 through the light path) by the lines 63 in which the filter region 61 is impervious to light or else has a very high light absorption, so that at the output of the light detector 58 there is obtained a pulse-like electric output signal X (digital measurement signal) in which the number of pulses corresponds to the distance by which the transmitter element 60 was moved in the direction of the double-ended arrow A relative to the transmitter element 53. With the filter region 61, the source of light 56 and the light detector 58, movement in two axes A and B which are perpendicular to each other and lie in the plane of the filter region 61 is thus possible, so that only two filter regions 61 and 62 are necessary in order to measure the relative movement in three axes A, B and C which are perpendicular to each other. In this way, a simplification of the transmitter element 60, is obtained as well, however, as the advantage that very large relative movements can be measured, particularly in axes A and B.

The light detectors 58 and 59 are connected to separate inputs of an amplifier device 64. The amplified output signal X and Y is available a the output of the amplifier device 64 and is fed to the input of a decoder 65. In the decoder 65, the analog measurement signal Y produced by the transmission wedge of the filter region 61 is separated from the digital measurement signal X produced by the lines 63. The analog measurement signal Y, as well as the analog measurement signal Z amplified in the amplifier device 64 is fed to tn analog-digital converter 66. The digital measurement signal X is fed to a digital evaluation device 67. At the output of the analog-digital converter 66 or the evaluation device 67 there are then available the measurement signals X, Y and Z, in each case in digital form, and they can be fed to a computer 68 for computing and/or evaluating the relative movement between the transmitter elements 53 and 60.

It is obvious that in an apparatus for the three-dimensional determination of the relative movement between a first and a second body, for instance for the three-dimensional determination of the movement of a lower jaw, two measurement transmitters 52 are used whose transmitter elements 63 are fastened to the upper yoke 1 in the same way as has been described for the transmitter element 8. The transmitter elements 60 are fastened to the lower yoke 3 in the same manner as has been described for the transmitter elements 28. The measurement signal X then corresponds to the movement in the horizontal axis, the measurement signal Y to the movement in the vertical axis, and the measurement signal Z to the movement in the transverse axis. The preparation of the measurement signals is effected for both measurement transmitters in the same way as shown in FIG. 13. In one measurement transmitter, the light path formed by the source of light 57 and the light detector 59 as well as the filter region 62 can be dispensed with.

I claim:

1. A device for the three-dimensional measurement of the relative movement between a first body and a second body, comprising two measurement transmitters spaced apart from each other, each said transmitter having a first transmitter element and a second transmitter element which is movable to said first transmitter element, said first transmitter elements being fastened to the first body using first means and said second transmitter elements being fastened to the second body using second means, each said measurement transmitters providing two measurement paths with a first of said two measurement paths on each said measurement transmitter being used for the determination of relative movement between the first and the second transmitter elements in a first axis, and with a second of said two measurement paths of each said measurement transmitter being used for the determination of relative movement between the first and the second transmitter elements in a second axis which is perpendicular to the first axis, at least one of said two measurement transmitters having an additional third measurement path, said additional third measurement path on said at least one measurement transmitter being used for the determination of relative movement between the first and the second transmitter elements of said at least one measurement transmitter having said additional third measurement path in a third axis that is perpendicular to said first and second axes, each said measurement path on each said measurement transmitters comprising a light path on the corresponding second transmitter element, each said light path being formed by a source of light, a light detector arranged at a distance from the source of light, said source of light and said light detector being on the second transmitter element, said light detector being an optoelectronic element creating an electrical output signal in response to the quantity or intensity of light striking the light detector, and optical filters on the first transmitter elements and lying within the light path between the light source and the light detector; the optical filters of the first and second measurement path on each of said two measurement transmitters, each filter including a transmission wedge having a filter density which increases or decreases in the direction in which the relative movement between the first and the second transmitter elements is determined by the corresponding measurement path such that, upon relative movement between the first transmitter element and the second transmitter element of said measurement transmitters in the first and/or second axis, the output signals of said light detectors of the first measurement paths vary in response to said relative movement in the first axis and the output signals of the light detectors of the second measurement paths vary in response to said relative movement in the second axis, respectively; the optical filter of the third measurement path on said at least one measurement transmitter being a dispersion screen such that, upon relative movement between the first transmitter element and the second transmitter element of said measurement transmitter having said third measurement path in the third axis, the output signal of the light detector of the third measurement path varies in response to said relative movement in the third axis; the optical filters on each first transmitter element lying in a common plane, and all light paths on each second transmitter element being parallel to each other.

2. A device according to claim 1, wherein said first axis is horizontal, said second axis is vertical and said third axis is a transverse axis perpendicular to said first and second axes.

3. A device according to claim 1, wherein said first body is the lower jaw the joint thereof of a patient and said second body is the head of a patient whereby the relative movement between the lower jaw or joints thereof and the head is determined in three dimensions.

4. A device according to claim 3, wherein said first means include a lower yoke having two side arms each of which bears said first transmitter element, and the second means include an upper yoke adapted to be fastened to the head of the patient, said upper yoke having two side arms each of which bear said second transmitter element cooperating said first transmitter element on the lower yoke.

5. A device according to claim 1, wherein each said first transmitter element of said at least two measurement transmitters has two filters, each filter includes a transmission wedge having a filter density which increases in an axial direction, said axial direction of one of the filters being perpendicular to the axial direction of the other filter.

6. A device according to claim 1, wherein said source of light and said light detector of at least one of said measurement transmitters are provided on the second transmitter elements that is adjustably mounted in two axial directions extending perpendicular to each other on said second means.

7. A device according to claim 4, wherein the second transmitter elements are adjustably mounted in two axial directions extending perpendicular to each other.

8. A device for the three-dimensional measurement of the relative movement between a first body and a second body, comprising two measurement transmitters spaced apart from each other, each said transmitter having a first transmitter element and a second transmitter element which is movable relative to said first transmitter element, the first transmitter elements being fastened to the first body using first means and said second transmitter element being fastened to the second body using second means, each said measurement transmitters providing one measurement path being used for the determination of relative movement between the first and the second transmitter elements in a first axis and a second axis which is perpendicular to the first axis, at least one of said two measurement transmitters having an additional second measurement path, said additional second measurement path on said at least one measurement transmitter being used for the determination of relative movement between the first and the second transmitter elements in a third axis that is perpendicular to said first and second axis, each said measurement path on each said measurement transmitters comprising a light path on the corresponding second transmitter element, each said light path being formed by a source of light, a light detector arranged at a distance from the source of light, said source of light and said light detector being on the second transmitter element, the light detector being an opto-electronic element creating an electrical output signal in response to the quantity or intensity of light striking the light detector, and an optical filter on the first transmitter elements lying within the light path between the light source and the light detector; the optical filter, of the first measurement path on each of said two measurement transmitters having a transmission wedge with a filter density which increases or decreases in one of the directions in which the relative movement between the first and the second transmitter elements is determined by the first measurement path and having a line pattern formed by a plurality of parallel light absorbing lines extending in said one direction so that, upon relative movement between the first transmitter element and the second transmitter element of said measurement transmitters in the second axis, the output signal of the light detector of the first measurement path varies in response to the relative movement in the second axis because of the increasing filter density of the transmission wedge, and upon relative movement between the first transmitter element and the second transmitter element of said measurement transmitters in the first axis, the output signal of the light detector of the first measurement path is an impulse-signal because of the light absorbing lines intersecting the corresponding light path, with the number of pulses being a function of the amount of movement in the first axis; the optical filter of the second measurement path on said at least one measurement transmitter being a dispersion screen such that upon relative movement between the first transmitter element and the second transmitter element of said measurement transmitter having said second measurement path in the third axis, the output signal of the light detector of the second measurement path varies in response to said relative movement in the third axis; the optical filters of the first transmitter element having said dispersion screen lying in a common plane, and all light paths on each second transmitter element being parallel to each other.

9. A device according to claim 8, wherein said first axis is horizontal, said second axis is vertical and said third axis is a transverse axis perpendicular to said first and second axis.

10. A device according to claim 8, wherein said first body is the lower jaw the joint thereof of a patient and said second body is the head of a patient whereby the relative movement between the lower jaw or joints thereof and the head is determined in three dimensions.

11. A device according to claim 10, wherein said first means include a lower yoke having two side arms each of which bears said first transmitter element, and the second means include an upper yoke adapted to be fastened to the head of the patient, said upper yoke having two side arms each of which bears said second transmitter element cooperating said first transmitter element on the lower yoke.

12. A device according to claim 8, wherein said source of light and said light detector of at least one of said measurement transmitters are provided on the second transmitter elements that are adjustably mounted in two axial directions extending perpendicular to each other on said second means.

13. A device according to claim 11, wherein the second transmitter elements are adjustably mounted in two axial directions extending perpendicular to each other.

* * * * *